United States Patent [19]

Bartlett et al.

[11] Patent Number: 4,824,190
[45] Date of Patent: Apr. 25, 1989

[54] CABINETRY DOOR AND TRANSPARENCY VIEWER

[75] Inventors: Randall N. Bartlett, Bay Minette, Ala.; Robert Case, Chicago, Ill.; John Sauls, Bay Minette, Ala.; Arden Jenkins, Bay Minette, Ala.; James McNew, Bay Minette, Ala.

[73] Assignee: Den-Tal-Ez, Inc., Philadelphia, Pa.

[21] Appl. No.: 515,009

[22] Filed: Jul. 18, 1983

[51] Int. Cl.⁴ ............................................. A47F 3/00
[52] U.S. Cl. .................................. 312/138 R; 40/361; 312/138 A; 312/323; 312/329
[58] Field of Search ................ 312/214, 138 R, 138 A, 312/109, 323, 322, 329, 257 R; 40/361, 363, 10.0, 574

[56] References Cited

U.S. PATENT DOCUMENTS

| | | | |
|---|---|---|---|
| 1,846,533 | 2/1932 | Thompson | 40/361 |
| 2,162,333 | 6/1939 | Golden | 312/214 X |
| 2,516,270 | 7/1950 | Swain | 40/361 |
| 2,760,288 | 8/1956 | Shoenfeld | 40/361 |
| 2,833,069 | 5/1958 | Cairns | 40/574 |
| 2,903,313 | 9/1959 | Schory et al. | 312/138 A |
| 2,936,206 | 5/1960 | Wilmer et al. | 312/222 |
| 3,044,841 | 7/1962 | Hein | 312/138 R |
| 3,598,463 | 8/1971 | Kesling | 312/138 R X |
| 3,722,971 | 3/1973 | Zeischegg | 312/109 X |
| 3,748,005 | 7/1973 | Chovanec et al. | 312/109 |
| 3,790,243 | 2/1974 | Whorton III | 312/214 |
| 4,185,406 | 1/1980 | Schotsman | 40/361 |
| 4,223,482 | 9/1980 | Barroero et al. | 312/138 R X |
| 4,261,125 | 4/1981 | Rappaport | 40/10 D X |
| 4,294,498 | 10/1981 | Van Luit | |

FOREIGN PATENT DOCUMENTS

| | | | |
|---|---|---|---|
| 126406 | 1/1948 | Australia | 312/329 |
| 821433 | 7/1949 | Fed. Rep. of Germany | 40/361 |
| 1041272 | 10/1958 | Fed. Rep. of Germany | . |
| 378144 | 9/1907 | France | . |
| 1059399 | 3/1954 | France | 40/361 |
| 1137833 | 6/1957 | France | . |
| 1172536 | 2/1959 | France | . |
| 1344373 | 10/1963 | France | . |
| 2024334 | 8/1970 | France | . |
| 2341493 | 9/1977 | France | 108/56.3 |
| 590578 | 4/1959 | Italy | 312/257 R |
| 633325 | 12/1949 | United Kingdom | . |
| 851488 | 10/1960 | United Kingdom | 312/214 |
| 903273 | 8/1962 | United Kingdom | 312/214 |

*Primary Examiner*—Kenneth J. Dorner
*Assistant Examiner*—Thomas A. Rendos

[57] ABSTRACT

A cabinetry door including a first member having a backwardly extending peripheral border and a second member having a forwardly extending peripheral border with a peripheral flange, wherein the peripheral flange of the second member is attached to the first member within its peripheral border. In a transparency viewer embodiment, the first member includes an light-transmitting portion and a transparency holder, and a light source is disposed between the first and second members.

11 Claims, 2 Drawing Sheets

U.S. Patent    Apr. 25, 1989    Sheet 1 of 2    4,824,190
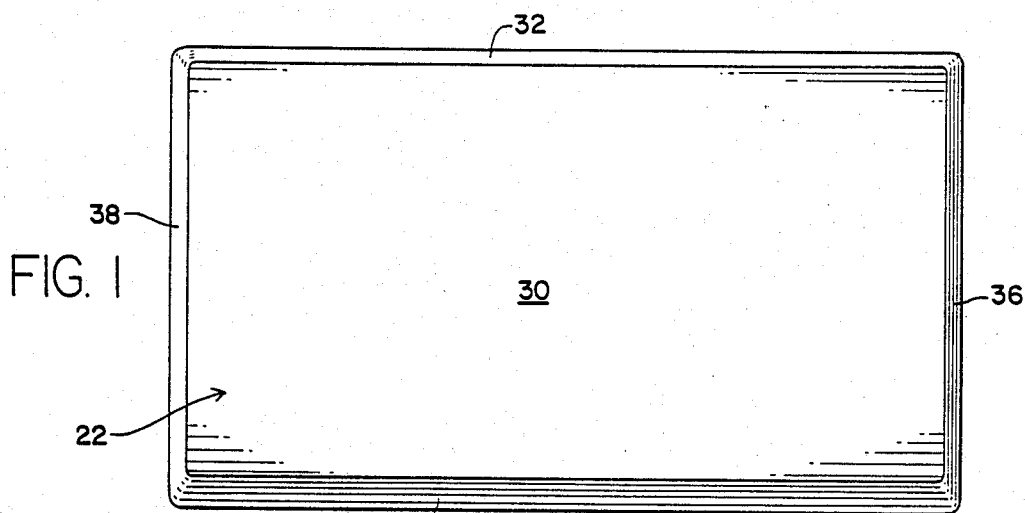
FIG. 1
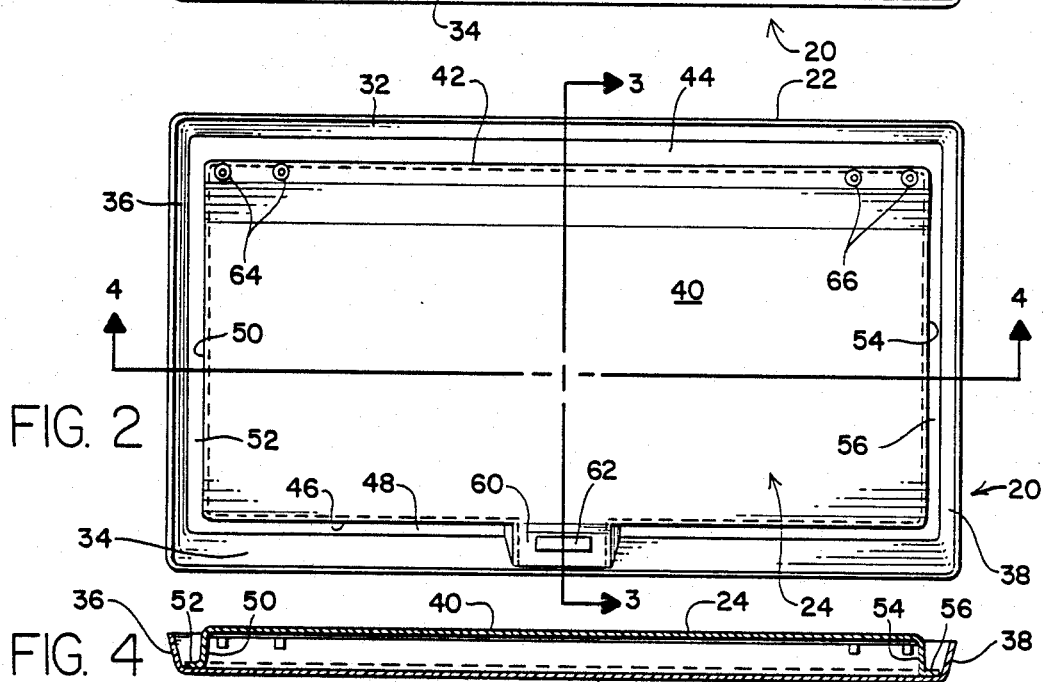
FIG. 2
FIG. 4
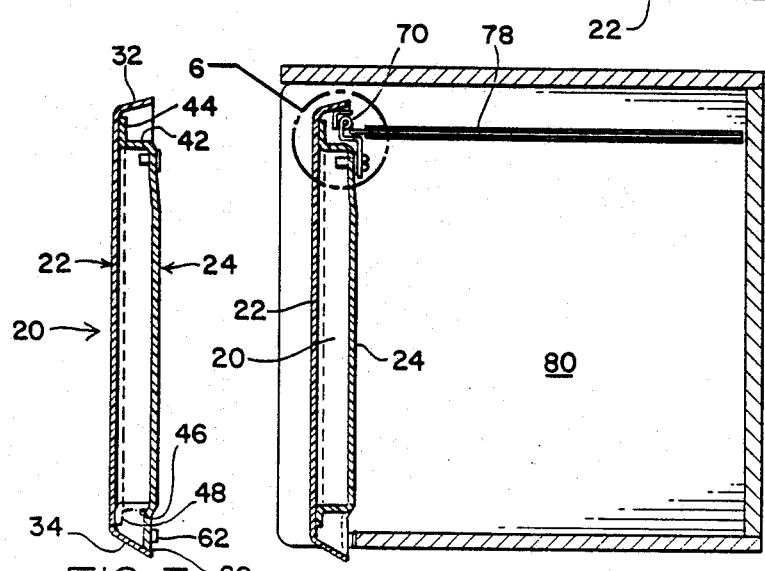
FIG. 3    FIG. 5
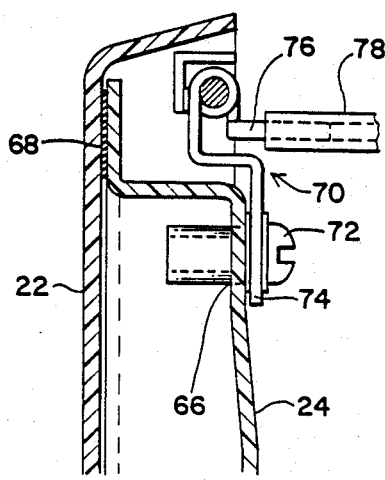
FIG. 6

CABINETRY DOOR AND TRANSPARENCY VIEWER

BACKGROUND OF THE INVENTION

The present invention relates to the field of closures, more particularly to a two-piece plastic construction for a cabinetry door. In one embodiment of the invention, the two-piece plastic construction may be used as a transparency viewer. A preferred use of the cabinetry door and transparency viewer of the invention in dental operatory settings.

The variety of door types and constructions is too great to discuss in detail. Materials such as wood, glass, metal, and thick sheets of plastic have all been used for cabinetry doors in the past. In many instances, the weight of such doors has been a problem due to the thickness required for maintaining structual rigidity and for receiving attachment hardware.

Another problem that has remained unsolved until the present invention has been the need for a separate unit for reading transparencies, for example, an X-ray viewer in a dental operatory. Such units take up counter or shelf space in the operatory that could otherwise be used as working surfaces. Also, the electrical requirements of such units limit their positionability and storage when not in use. An object of the present invention is to provide a two-piece, hollow construction for a cabinetry door.

Another object of the invention is to provide a lightweight cabinetry door that can swing up and be slid back into a cabinet.

Yet another object of the invention is to provide a lightweight cabinetry door that is partially transparent to provide partial visibility for the contents of the cabinet from the outside without opening the door.

The further object of the invention is to provide a two-piece plastic cabinetry door that is easy and inexpensive to manufacture, lightweight, structurally rigid, and is somewhat transparent for viewing contents of a cabinet.

Another object of the invention is to provide a transparency viewer that can be lifted up and slid under a cabinet or shelf to be out of the way.

Still another object of the invention is to provide a transparency viewer that may be attached to the bottom of a shelf or cabinet to be lifted up and slid out of the way when not in use, and also serve as a task light for a work surface under it when it is in the stored position.

A still further object of the invention is to provide a cabinet door and transparency viewer.

Yet another object of the invention is to provide a cabinet door and transparency viewer wherein said door may serve as a transparency viewer when in the down position and may serve as a task light or cabinet light when in the up position.

Other objects, advantages and features of the present invention will become apparent with reference to the following description of the preferred embodiments and the appended claims and drawings.

SUMMARY OF THE INVENTION

A cabinetry door includes two members. A first member has a planar main surface with a top surface, a bottom surface, a right side surface and a left side surface forming a peripheral lip around the main surface. The second member has a planar main surface, also with a peripheral lip. A top parallel surface, bottom parallel surface, right side parallel surface and left side parallel surface form a peripheral flange about the second member's peripheral lip. The flange is received by the planar main surface in the first member. Securing means connect the second member to the first member.

In a transparency viewer embodiment of the invention, the first member has a light-transmitting portion associated with its planar main surface. Holding members are provided to hold transparencies against the light-transmitting portion. A light source is disposed between the first and second members, the second member being provided with an access opening having a removable cover.

DESCRIPTION OF THE DRAWINGS

In the drawings:

FIG. 1 is a front elevational view of a cabinetry door embodying the principles of the present invention;

FIG. 2 is a back elevational view of a cabinetry door embodying the principles of the present invention;

FIG. 3 is side elevational view of a cabinetry door embodying the principles of the present invention, taken in section along line 3—3 in FIG. 2;

FIG. 4 is an elevational view of a cabinetry door embodying the principles of the present invention, taken in section along line 4—4 in FIG. 2.

FIG. 5 is a sectional elevational view of a cabinetry door embodying the principles of the present invention illustrated installed in a cabinet and shown in the down position;

FIG. 6 is an enlarged section of the attachment portion (illustrated within the circle in FIG. 5) of a cabinetry door embodying the principles of the present invention;

DETAILED DESCRIPTION OF THE PREFERRED EMBODIMENTS

Figure 7:
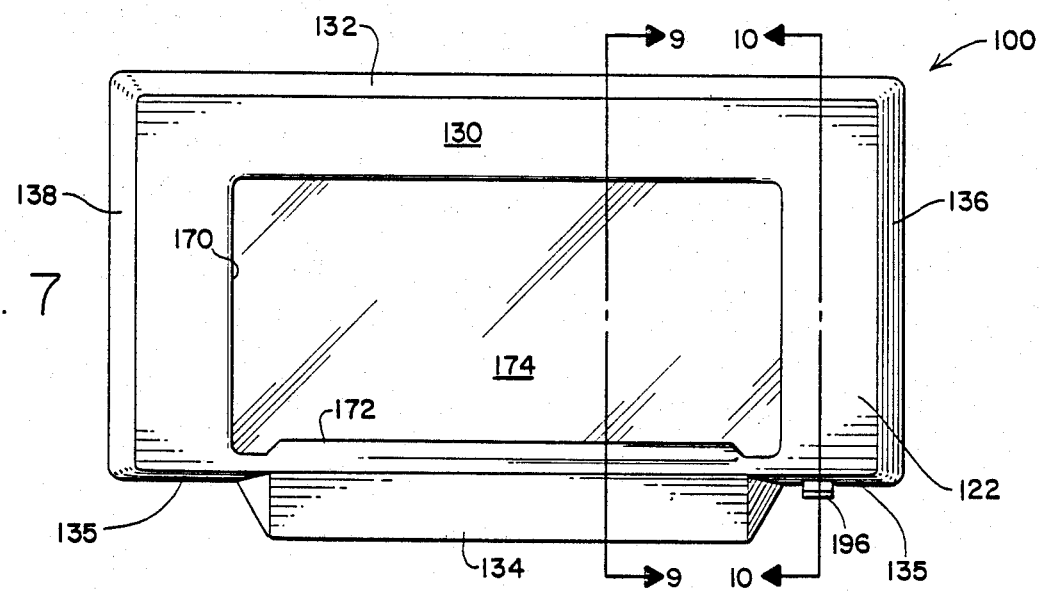
FIG. 7 is a front elevational view of a cabinetry door and transparency viewer embodying the principles of the present invention.

A cabinetry door 20 in accordance with the present invention has a front member 22 and a back member 24. Both the front and back members may be made of a moldable plastic material (such as lexan) and are preferably vacuum formed to their respective shapes. As shown in FIG. 1, front member 22 has the general shape of a shallow rectangular tub, having a planar front surface 30, and a peripheral lip formed by a slanted top surface 32, a slanted bottom surface 34, a slanted right side surface 36 and a slanted left side surface 38. The outside (front) surface of front member 22 preferably has a roughened, scratch-resistant finish. Referring to FIGS. 2, 3 and 4, back member 24 has a back planar surface 40, a top perpendicular surface 42, a top parallel surface 44, a bottom perpendicular surface 46, a bottom parallel surface 38, a right side perpendicular surface 50, a right side parallel surface 52, a left side perpendicular surface 54 and a left side parallel surface 56. An extended portion 60 of back planar surface 24 is provided with a securing member 62 such as the plate for a magnetic catch, or a portion of a mechanical latch.

The perpendicular surfaces 42, 46, 50 and 54 form a peripheral lip. The parallel surfaces 44, 48, 52 and 56 form a peripheral flange around the back member which corresponds to the peripheral area of front surface 30, so that the back member 24 may be placed within the front member 22 and secured to it by means such as an adhesive 68, double-sided tape, glue, cement, velcro, or a mechanical fastener. It is preferred to use double-sided tape.

Two pairs of openings 64 and 66 are provided at the top right and left corners of back planar surface 40 for the attachment of hinges 70 by attachment means 72 such as a nut and bolt, a molly, or preferably an expanding bolt such as the "Plus-Nut" (sold by B. F. Goodrich). The hinge (as illustrated in FIGS. 5 and 6) has two portions, a first portion 74 that is attached to the back member 24, and a second portion 76 that is received within a track 78 affixed inside a cabinet 80 in which the door 20 is installed. The door 20 is thus movable from its lowered position as shown in FIG. 5 to a stored or open position by swinging the door up parallel to the cabinet top and sliding it back along the track 78.

Figure 8:
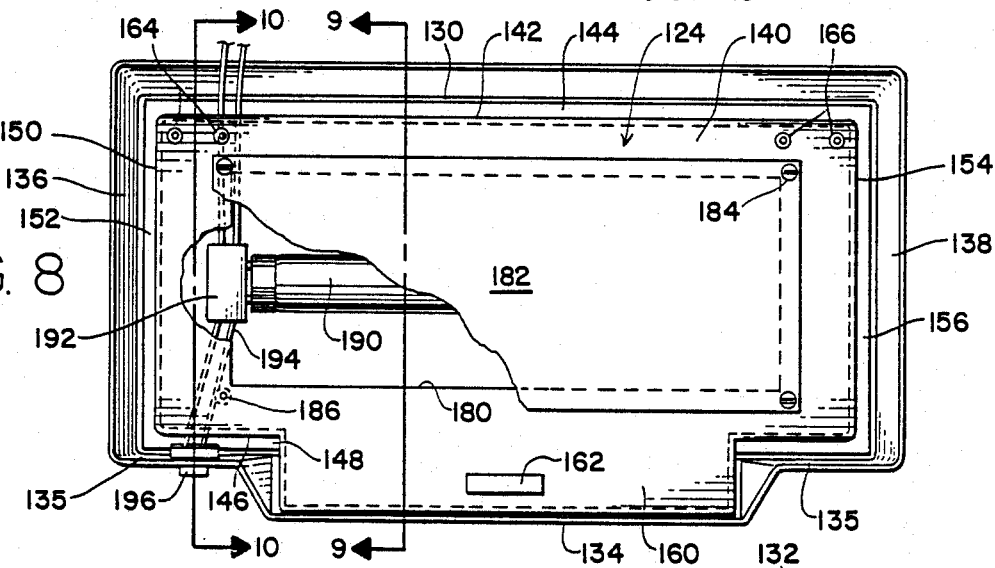
FIG. 8 is a back elevation view of a cabinetry door and transparency viewer embodying the principles of the present invention, a portion of the back cover being broken away to better illustrate the lighting means.
Figure 9:
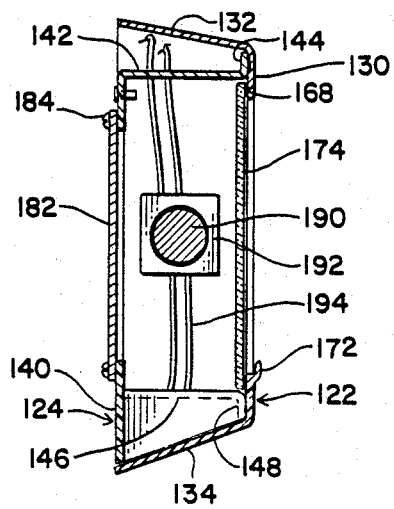
FIG. 9 is a sectional view of a cabinetry door and transparency viewer embodying the principles of the present invention, taken along line 9—9 in FIG. 7.
Figure 10:
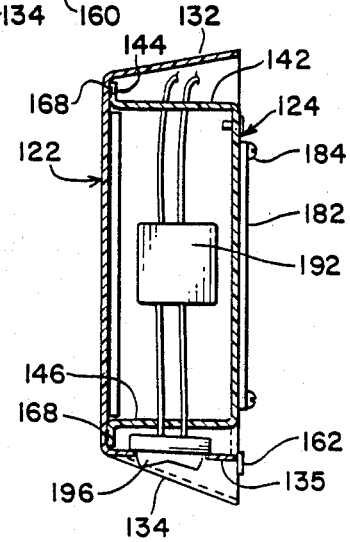
FIG. 10 is a sectional view of a cabinetry door and transparency viewer embodying the principles of the present invention, taken along line 10—10 in FIG. 7.

A cabinetry door and transparency viewer 100 of the present invention, as illustrated in FIGS. 7-10, is similar both in construction and mounting to the cabinetry door 20. The door and viewer 100 may be used as a cabinet closure, such as the door 20, or may be used as a separate device suspended from beneath a cabinet to provide task lighting when in the up or stored position and to view transparencies such as X-rays when in the down position.

Front member 122 and back member 124 are secured together in the same fashion as are front member 22 and back member 24, by use of securing means such as an adhesive 168, double-sided tape, glue, cement, velcro or a mechanical fastener.

Front member 122 has a front surface 130, a slanted top surface 132, a slanted bottom surface 134 having two recessed end portions 135, a slanted right side surface 136, and a slanted left side surface 138.

Back member 124 has a back planar surface 140, a top perpendicular surface 142, a top parallel surface 144, a bottom perpendicular surface 146, a bottom parallel surface 148, a right side perpendicular surface 150, a right side parallel surface 152, a left side perpendicular surface 154 and a left side parallel surface 156. Back planar surface 140 also has an extended portion 160 for a securing member 162, and has two pair of hinge openings 164 and 166 at the upper right and left corners, respectively.

Front member 122 has a cutaway portion 170 in front planar surface 130, which is provided with a protruding portion 172 at the bottom of cutaway portion 170 to serve as a transparency holder. A light-transmitting portion has a translucent panel 174 disposed behind front planar surface 130 and surrounding cutaway portion 170; the translucent panel is adhered to the back of front member 122 by securing means 168, smilar to the means used for attachment of back member 124.

The back planar surface of back member 124 also has a cutaway portion 180 which is covered by a light transmitting panel 182, the panel being attached by members 184, such as screws, which are received in openings 186 disposed in back planar surface 140. A replaceable bulb 190 and its associated fixture 192 are disposed between front member 122 and back member 124, as, by example, by fastening to the front surface of back member 124. The fixture is provided with wiring 194 leading to a switch 196 disposed in recessed portion 135 and to a power source (not shown).

To those skilled in the art to which this invention relates, many changes in construction and widely differeing embodiments and applications of the invention will suggest themselves without departing from the spirit and scope of the invention. For example, changes in the overall shape of the door, its size, and the materials from which it is constructed are easily made and are intended to be covered as part of the present invention. The disclosure and descriptions herein are purely illustrative and are not intended to be in any sense limiting.

What is claimed is:

1. A cabinetry door and transparency viewer, adapted to being swung up and slid back into the upper part of a cabinet along tracks provided therein, which comprises:
   a first member forming the front of the door, the first member having a planar main surface and a backwardly extending peripheral lip surrounding the main surface, the main surface having a light transmitting portion comprising a cutaway portion in the main surface and a panel of translucent material disposed adjacent the cutaway portion, and a transparency holding means for supporting a transparency against the light transmitting portion which comprises a forwardly extending lip at a bottom edge of the cutaway portion;
   a second member forming the back of the door, the second member having a planar main surface, a forwardly extending peripheral lip surrounding the main surface, and a peripheral flange parallel to the main surface surrounding the peripheral lip;
   illumination means, disposed between the first and second members, for providing light to the light transmitting portion;
   securing means for attaching the front of the peripheral flange of the second member to the rear of the main surface of the first member; and
   at least one hinge attached adjacent an upper edge of the main surface of the second member and adapted for engagement with the tracks of the cabinet to allow the door to be swung up and slid back into the cabinet;
   whereby the door may also be used as a transparency viewer when it is not slid back into the cabinet.

2. The cabinetry door of claim 1, wherein the second member includes:
   a coplanar extension of the main surface, the extension being disposed from a junction between the main surface and a bottom angled surface of the peripheral lip to a position approximating a bottom surface of the peripherqal lip of the first member when the first and second members are assembled together, and
   closure means on the extension.

3. The cabinetry door of claim 2, wherein the closure means comprises a strip of magnetic material.

4. The cabinetry door of claim 1, wherein the illumination means comprises a fluorescent lamp and fixture.

5. The cabinetry door of claim 1, wherein the main surface of the second member includes a cutaway portion for providing access to the illumination means, and a removable panel to cover the cutaway portion.

6. The cabinetry door of claim 1, wherein the first and second members are made of a plastic material.

7. A cabinetry door, transparency viewer, and task light, adapted to being swung up and slid back into the upper part of a cabinet along tracks provided therein, which comprises:
- a first member forming the front of the door, the first member having a planar main surface and a backwardly extending peripheral lip surrounding the main surface, the main surface having a light transmitting portion comprising a cutaway portion in the main surface and a panel of translucent material disposed adjacent the cutaway portion, and a transparency holding means for supporting a transparency against the light transmitting portion which comprises a forwardly extending lip at a bottom edge of the cutaway portion;
- a second member forming the back of the door, the second member having a planar main surface, a forwardly extending peripheral lip surrounding the main surface, and a peripheral flange parallel to the main surface surrounding the peripheral lip, the main surface having a light transmitting portion comprising a cutaway portion in the main surface and a removable panel of transparent material disposed adjacent the cutaway portion;
- illumination means, disposed between the first and second members, for providing light to the light transmitting portions;
- securing means for attaching the front of the peripheral flange of the second member to the rear of the main surface of the first member; and
- at least one hinge attached adjacent an upper edge of the main surface of the second member and adapted for engagement with the tracks of the cabinet to allow the door to be swung up and slid back into the cabinet;
- whereby the door may be used as a transparency viewer when it is not slid back into the cabinet and may be used as a task light when it is slid back into the cabinet.

8. The cabinetry door of claim 7, wherein the second member includes:
- a coplanar extension of the main surface, the extension being disposed from a junction between the main surface and a bottom angled surface of the peripheral lip to a position approximating a bottom surface of the peripheral lip of the first member when the first and second members are assembled together, and
- closure means on the extension.

9. The cabinetry door of claim 8, wherein the closure means comprises a strip of magnetic material.

10. The cabinetry door of claim 7, wherein the illumination means comprises a fluorescent lamp and fixture.

11. The cabinetry door of claim 7, wherein the first and second members are made of a plastic material.

* * * * *